United States Patent
Dowd et al.

(10) Patent No.: US 6,321,103 B1
(45) Date of Patent: Nov. 20, 2001

(54) FETAL SPIRAL ELECTRODE SLEEVE AND WIRE INTERCONNECT SYSTEM

(75) Inventors: Edward Dowd, Mallorytown (CA); Robert J. Graumann, West Hartford, CT (US); Brian E. Haug, Portland; James F. McIntire, West Linn, both of OR (US); Joseph T. O'Neill, Kingston (CA)

(73) Assignee: The Ludlow Company LP, Chicopee, MA (US)

( * ) Notice: Subject to any disclaimer, the term of this patent is extended or adjusted under 35 U.S.C. 154(b) by 0 days.

(21) Appl. No.: 09/533,259

(22) Filed: Mar. 21, 2000

(51) Int. Cl.[7] .................................. A61B 5/0448
(52) U.S. Cl. .................. 600/376; 600/511; 439/669; 439/675; 439/909
(58) Field of Search .................. 600/376, 511; 607/119, 122, 127; 439/909, 669, 675

(56) References Cited

U.S. PATENT DOCUMENTS 5,277,613 * 1/1994 Neward ........................... 439/909
6,151,520 * 11/2000 Combs ........................... 600/376

FOREIGN PATENT DOCUMENTS 3326128   1/1985 (DE) .

OTHER PUBLICATIONS

International Search Report dated Jul. 31, 2001.

* cited by examiner

Primary Examiner—Linda C. M. Dvorak
Assistant Examiner—David M. Ruddy
(74) Attorney, Agent, or Firm—Ratner & Prestia

(57) ABSTRACT

A fetal electrode sleeve and wire interconnect system for transmitting signals indicative of fetal heart rate from a fetus inside a mother through a cable to a monitor external to the mother. The system includes a holder having a fetal spiral electrode on one end and a maternal reference electrode on its opposite end. A safety cap has a retention groove, a grip, a tip with a recessed end opposite the grip, and a conductive sleeve. The conductive sleeve has a first end enclosed by the grip, a second end enclosed by the tip, and an intermediate exposed portion enclosed by neither the grip nor the tip. A twisted wire strand including a pair of insulated wires each having a first end and a second end, the first ends of the wires respectively connected to the fetal electrode and the maternal reference electrode, the second end of one wire attached to the first end of the conductive sleeve and the other wire being disposed inside the conductive sleeve, extending beyond the second end of the conductive sleeve, and terminating at its second end as a bare and exposed wire at the recessed end of the tip so that the second end of the wire is protected. A housing receives the safety cap and facilitates electrical connection between the wires and the cable.

30 Claims, 5 Drawing Sheets

FETAL SPIRAL ELECTRODE SLEEVE AND WIRE INTERCONNECT SYSTEM

TECHNICAL FIELD

The present invention relates generally to systems used to monitor the health of a fetus during labor and deliver and, more particularly, to an interconnection arrangement for safely monitoring fetal heart rate. The arrangement electrically interconnects a remote fetal monitor with bipolar fetal electrodes.

BACKGROUND OF THE INVENTION

It is desirable to monitor the biological functions (such as heart rate) of a fetus continuously during labor and delivery in order to detect fetal distress. Devices which are external to the mother's body are insufficiently sensitive. In the case of heart rate signals, such devices do not adequately isolate the fetal and maternal heartbeats. Consequently, devices which attach directly to the fetus during labor are used. U.S. Pat. No. Re. 28,990, issued to Hon et al., discloses a fetal spiral electrode assembly historically used to monitor fetal heart rate during birth.

The conventional fetal spiral electrode assembly includes a curved guide tube of adjustable shape for insertion of the fetal spiral electrode through the mother's cervix and into contact with the fetus during labor. A nonconductive plastic tip or holder is slidably received in the guide tube. A sharp, pointed, fetal spiral electrode is mounted on the forward end of the holder for contacting the fetal epidermis.

A reference (maternal) electrode in the form of a flat fin or plate is electrically isolated from the fetal electrode and located on the rear end of the holder. A flexible, hollow drive tube with a cutout on its forward end fits inside the guide tube and engages the holder. The drive tube has a diameter smaller than the diameter of the guide tube. The cutout of the drive tube engages the reference electrode in the holder to impart translation and rotation to the holder and, hence, to the fetal spiral electrode. A handle on the opposite end of the drive tube allows the user to push, pull, and rotate the drive tube within the guide tube. A forward-twisting force is applied to the drive tube to affix the fetal spiral electrode in the fetal epidermis.

The two electrodes are connected to separate wires which are threaded through the common center of the drive and guide tubes until they ultimately exit at the rear end of the drive tube. The wires connected to the electrodes are twisted about each other so that any induced voltages caused by external electromagnetic interference will be the same in each and therefore will not adversely affect the measurement of the galvanic potential difference between the electrodes. After the fetal spiral electrode is secured to the fetal epidermis, the drive tube and guide tube are removed by pulling the tubes longitudinally over the wires and away from the mother. Removal of the drive and guide tubes leaves the electrodes, the holder, and the wires in place inside the mother. The bare, uninsulated ends of the wires are then connected, via an intermediate support or leg plate, to a fetal monitor.

To use the fetal spiral electrode product, the shape of the guide tube is adjusted and the guide tube is inserted through the mother's cervix and into contact with the fetus. Once the guide tube contacts the fetus (and is held against the fetus using one of the user's hands), the drive tube is advanced (using the second hand) until the fetal spiral electrode contacts the fetus. While pressure is maintained against the fetus by the guide tube and drive tube, the drive tube is rotated, using the second hand and the handle, until the fetal spiral electrode is secured to the fetal epidermis. Typically, one full revolution suffices to secure the fetal spiral electrode. Then the drive tube and guide tube are removed by sliding them over the electrode wires.

U.S. Pat. No. 5,680,859 issued to Urion et al. is an improvement over the device disclosed in the '990 patent. Manual connection of the uninsulated ends of the wires is cumbersome and risks shorting the wires. If shorted, the wires cannot transmit correct signals from the fetal and reference electrodes. Accordingly, the '859 patent adds a connector to the wire ends of the fetal spiral electrode assembly disclosed in the '990 patent.

FIG. 6 is a side view of the fetal spiral electrode system 110 disclosed by Urion et al. Electrode system 110 includes a sharp, pointed fetal spiral electrode 120 for contacting the fetal epidermis; a reference (maternal) electrode 122 in the form of a flat fin or plate which is electrically isolated from fetal spiral electrode 120; a holder 124; and two electrode wires 126a and 126b.

Holder 124 is an electrically insulating plastic and is adapted to be slidably received inside an introducer 140. Fetal spiral electrode 120 is mounted on the forward end of holder 124. Reference electrode 122 is attached to the rearward end of holder 124.

A drive rod 130 is slidably received in introducer 140. Drive rod 130 has a clutch 128 at its forward end. Clutch 128 engages reference electrode 122 in holder 124 to impart translation and rotation to holder 124 and, hence, to fetal spiral electrode 120. A handle 150 on the opposite end of drive rod 130 allows the user to push, pull, and rotate drive rod 130. Drive rod 130, clutch 128, and handle 150 are integrally molded together.

Electrode wires 126a and 126b are separately coupled to respective electrodes 120 and 122. Electrode wire 126a (typically green in color) connected to fetal spiral electrode 120 and electrode wire 126b (typically red) connected to reference electrode 122 form a twisted wire strand 118 which extends from electrodes 120 and 122 along the entire length of drive rod 130 and handle 150. A retainer 166 is provided near the end of handle 150 opposite drive rod 130. Retainer 166 locks wire strand 118 in a fixed position. The ends of wires 126a and 126b opposite holder 124 terminate in a male connector 132.

Turning to FIG. 7, wires 126a and 126b (which are typically about 450 mm or 18 inches in length) are provided with an untwisted length 116 along a short distance (25–50 mm or 1–2 inches) of wire strand 118. Untwisted length 116 allows the clinician to separate wires 126a and 126b without cutting them. The individual wires 126a and 126b are separately connected to first and second terminal (or ring) contacts 134 and 136 in connector 132. Contacts 134 and 136 are electrically and physically separated by a spacer 138. Connector 132 has a forward tapered tip 142 which plugs into a longitudinal passage in the end of handle 150 (connector 132 is shown plugged into the passage in FIG. 6).

Connector 132 is designed to be inserted into a support or leg plate 170 which is affixed to the mother (typically to the thigh). Support plate 170 is connected, via a cable 176, to a monitor 178. Upon insertion of connector 132 into the opening of support plate 170, ring contacts 134, 136 on connector 132 click into physical and electrical contact with two corresponding barrel contacts in support plate 170. Moreover, tip 142 of connector 132 abuts a wall in support plate 170 to prevent over-insertion of connector 132.

Support plate 170 carries its own ground electrode 180. Insertion of connector 132 in support plate 170 connects electrodes 120 and 122 to monitor 178. Consequently, three electrical circuit paths are created upon interconnection of connector 132 of fetal spiral electrode system 110 and support plate 170: (1) fetal electrode 120 to green wire 126*a* to terminal 134 to a first barrel contact to a first output terminal to monitor 178; (b) reference electrode 122 to red wire 126*b* to terminal 136 to a second barrel contact to a second output terminal to monitor 178; and (c) ground electrode 180 to a third output terminal to monitor 178.

Connector 132 has a grip 144 with an ergonomically designed shape to permit the user to grasp it easily and to ensure a proper, sealed connection of connector 132 to support plate 170. Grip 144 also acts as a strain relief element through which twisted wire strand 118 enters connector 132. The diameter of connector 132 changes, at a shoulder 146, from a smaller diameter plug 148 to larger diameter grip 144. The length of smaller diameter plug 148 is selected to correspond to the length by which connector 132 must be inserted fully into support plate 170 to assure optimal signal quality. Thus, connector 132 permits a visual indication of full attachment of connector 132 to support plate 170.

Connector 132 solves the problem of manual connection of the uninsulated ends of the electrode wires. But the connector 132 with its exposed first and second terminal (or ring) contacts 134 and 136 does not prevent entirely the risk of accidental electrocution of patients by having an exposed contact engage a hazardous voltage. Such prevention is not only desirable, it is now mandated by the U.S. government and by international standards.

The "Performance Standard for Electrode Lead Wires and Patient Cables" of the Code of Federal Regulations, Chapter 21, Part 898, states that, beginning on May 9, 2000, all fetal scalp electrodes and associated cable systems must comply with the standard. In summary, this performance standard is designed to prevent accidental electrocution of patients by precluding an exposed lead or contact that might come into contact with a hazardous voltage. Consequently, leads and contacts must be constructed to prevent accidental patient contact with hazardous voltages and, after May 9, 2000, unprotected electrode lead wires and cables cannot be manufactured, distributed, or sold in the United States. Existing leads and contacts on fetal spiral electrode products currently sold in the United States market are non-compliant because the leads and contacts are exposed. Specifically, the current fetal spiral electrode designs have either two bare wires or exposed contacts that could potentially come into contact with an electrical source when not connected to the support or leg plate.

If a lead or contact may be placed on a conductive surface or inserted into an electrical socket, hazardous voltages could occur. Alternatively, if a user can run a finger over the lead or contact and can touch metal, the lead is considered non-compliant under the governmental standard. For a lead or contact to comply with the standard, it must preclude contact with hazardous voltages and pass specific tests.

There are approximately 45,000 fetal monitors in the United States and approximately three million fetal spiral electrodes are used per year. The deficiencies of the conventional devices and the market demand show that a tremendous need exists for an improved fetal spiral electrode interconnect system that functions to electrically and mechanically connect the conventional twisted wire pair with the cable to the remote fetal monitor. To overcome the shortcomings of conventional fetal spiral electrode systems, an integrated fetal electrode sleeve and wire system is provided. The principal object of the present invention is to provide an improved system that is fully compliant with governmental performance standards. An important related object is to provide a system that reduces safety risks, especially the risk of inadvertent connection to an electrical source. Another object is to provide a system that provides both safe and reliable tracing of fetal heart rate to help caregivers deliver the best patient care.

SUMMARY OF THE INVENTION

To achieve these and other objects, and in view of its purposes, the present invention provides a fetal electrode sleeve and wire interconnect system for monitoring signals indicative of fetal heart rate from a fetus inside a mother during labor and delivery. The system comprises a cable having a maternal lead, a fetal lead, and a ground lead. A holder has a fetal spiral electrode on one end and a maternal reference electrode on its opposite end. The system also comprises a ground electrode secured to the mother, particularly to the leg of the mother, preferably using an adhesive. A safety cap has a retention groove, a grip, a tip opposite the grip with a shroud defining both a safety cap terminus and an end recessed relative to the terminus, and a conductive sleeve. The grip of the safety cap has a plurality of cutouts disposed opposite the tip, the cutouts providing strain relief to and increasing the flexibility of the safety cap and being adapted to facilitate handling of the safety cap by the user. The conductive sleeve includes a first end enclosed by the grip, a second end enclosed by the tip, and an intermediate exposed portion enclosed by neither the grip nor the tip. A twisted wire strand is formed by a pair of insulated wires each having a first end and a second end, the first ends of the wires respectively connected to the fetal electrode and the maternal reference electrode, the second end of one wire attached to the first end of the conductive sleeve and the other wire being disposed inside the conductive sleeve, extending beyond the second end of the conductive sleeve, and terminating at its second end as a bare and exposed wire at the recessed end of the tip so that the second end of the wire is protected within the shroud.

The housing of the fetal electrode sleeve and wire interconnect system has an aperture receiving the safety cap, without restriction relative to the orientation of the safety cap, and an opening receiving the cable. A retaining element engages the retention groove in the safety cap upon insertion of the safety cap in the aperture of the housing and releasably holds the safety cap in the housing. A snap is connected to the ground electrode and attached to the ground lead of the cable. The housing rotates without restriction relative to the ground electrode. A guide of the housing at least partially encircles the snap and includes an alignment channel receiving and aligning the tip of the safety cap upon insertion of the safety cap into the housing. An axial contact element is aligned in the channel of the guide and attached to the maternal lead of the cable, the axial contact element axially engaging the tip of the safety cap and contacting the bare and exposed wire upon insertion of the safety cap into the housing. The housing also has a radial contact element including at least one finger, the finger radially engaging the intermediate exposed portion of the conductive sleeve of the safety cap upon insertion of the safety cap into the housing thereby electrically contacting the conductive sleeve, the radial contact element also being attached to the fetal lead of the cable. Finally, the housing may have a rubber O-ring positioned in the aperture of the housing and through which the safety cap is inserted into the housing, the ring wiping the safety cap upon insertion.

The fetal electrode sleeve and wire interconnect system also comprises a monitor connected to the cable. A drive mechanism imparts rotation and translation to the holder to secure attachment of the fetal spiral electrode to the fetus. An introducer is disposed around at least a portion of the drive mechanism and can be comfortably inserted through the cervix of the mother. The holder is slidably and rotatably disposed in the introducer.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
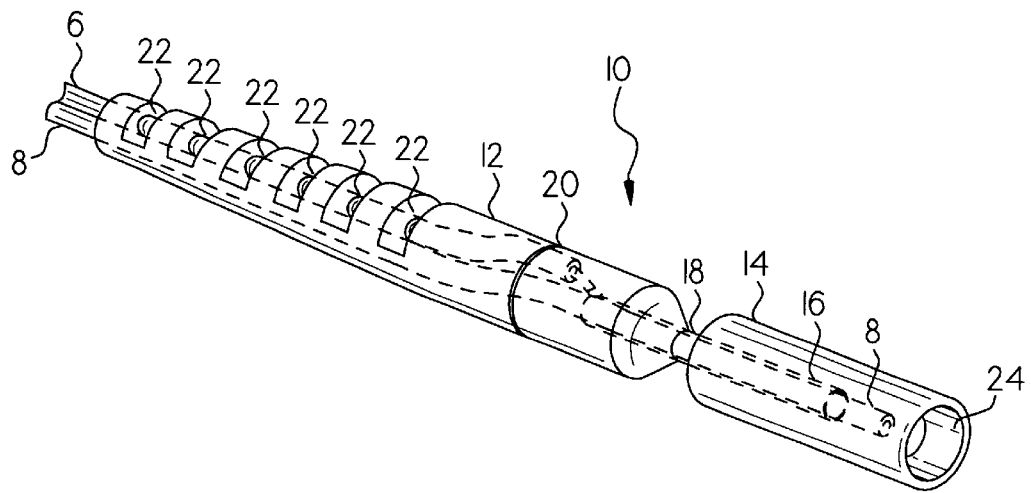
FIG. 1 is a perspective view of the safety cap in accordance with the present invention.

Referring now to the drawing, in which like reference numbers refer to like elements throughout, FIG. 1 is a perspective view of a safety cap 10 having three, main components: a grip segment 12, a tip segment 14, and a conductive sleeve 16 extending axially (or longitudinally) through the centers of grip segment 12 and tip segment 14. Conductive sleeve 16 is typically about 1.5 mm in diameter and made of a gold-plated brass tube. As shown in dashed lines in FIG. 1, conductive sleeve 16 has a first end enclosed by grip segment 12, extends partially (about halfway as shown) into tip segment 14, and has a second end enclosed by tip segment 14.

Figure 6:
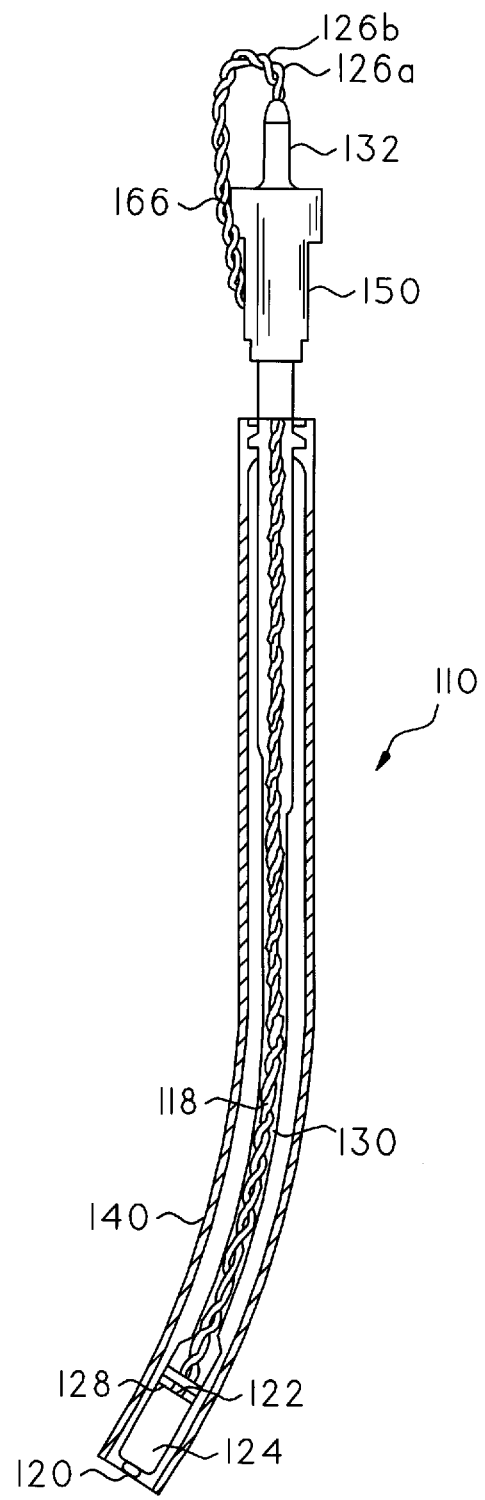
FIG. 6 is a side view of a conventional fetal spiral electrode system.

The insulated wire 6 of the twisted wire pair that engages the fetal spiral electrode 120 (see FIG. 6) is attached (e.g., welded) to the end of conductive sleeve 16 within grip segment 12. Grip segment 12 and tip segment 14 are preferably molded around conductive sleeve 16 while leaving an exposed portion 18 of conductive sleeve 16. Exposed portion 18 is enclosed by neither grip segment 12 nor tip segment 14. A retention groove or detent 20 is provided in safety cap 10. Retention groove 20 may be provided in grip segment 12, as shown, or in tip segment 14 of safety cap 10. A series of cutouts 22 (six are shown in FIG. 1) are formed in the end of grip segment 12 opposite tip segment 14 to provide strain relief, increase flexibility, and facilitate the grip of the user.

The end 24 of tip segment 14 opposite grip segment 12 is recessed, creating a shroud that defines both a terminus for safety cap 10 and an end recessed relative to that terminus. The insulated wire 8 of the twisted wire pair that engages the maternal electrode 122 (see FIG. 6) travels through conductive sleeve 16 and terminates, without any separate connector component, as a bare and exposed wire in recessed end 24. More specifically, wire 8 extends beyond the second end of conductive sleeve 16 and terminates at its second end (opposite the first end which is attached to maternal electrode 122) as a bare and exposed wire at the recessed end 24 of tip segment 14 so that the second end of wire 8 is protected within the shroud. Therefore, conductive sleeve 16 is the only contact or terminal engaged by wires 6, 8, and only wire 6 is electrically and mechanically connected to conductive sleeve 16. Recessed end 24 assures that safety cap 10 meets safety regulations by preventing inadvertent and undesired contact with wire 8. Because both wires 6, 8 are encapsulated within single molded plastic safety cap 10, safety cap 10 avoids exposed electrode wires or contacts.

Figure 2:
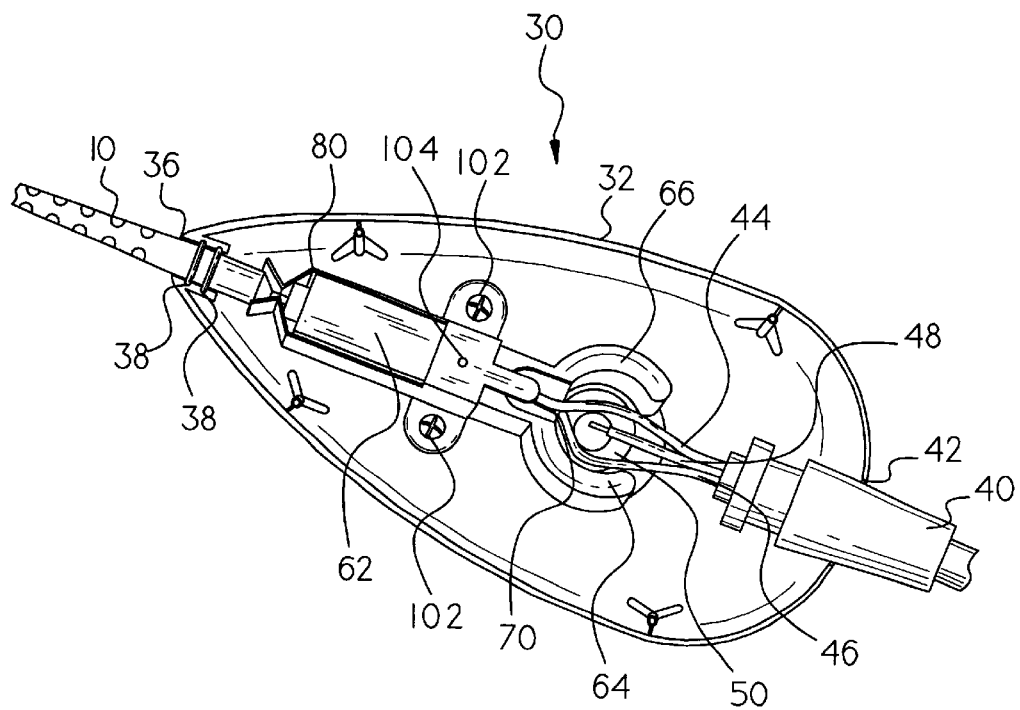
FIG. 2 is a top perspective view of the bottom half of the housing, with engaged components, according to the present invention.
Figure 3:
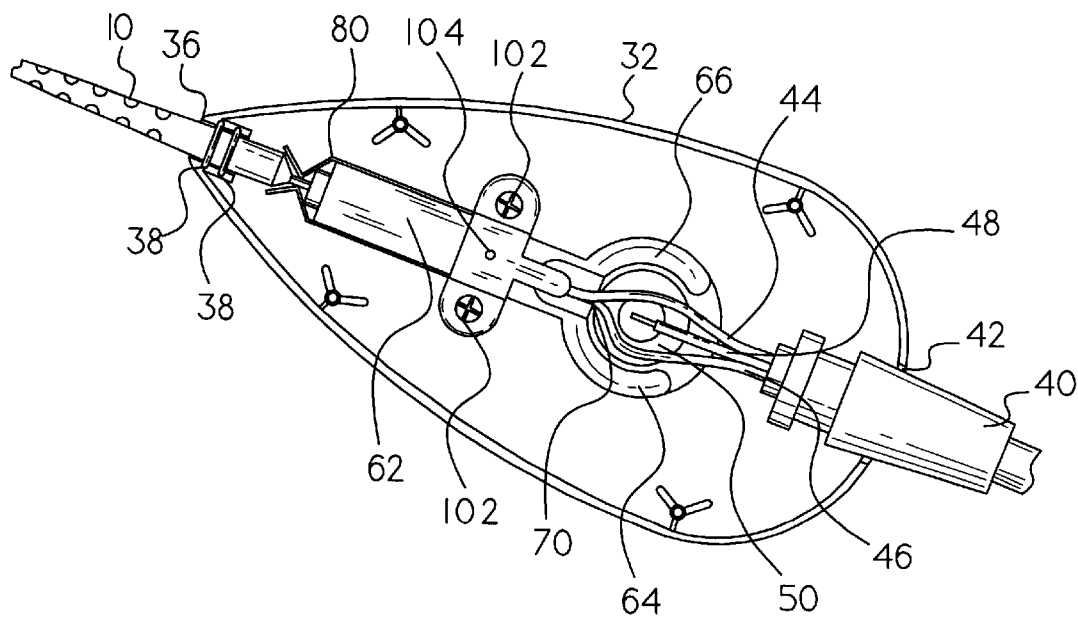
FIG. 3 is a top view of the housing and engaged components illustrated in FIG. 2.
Figure 5:
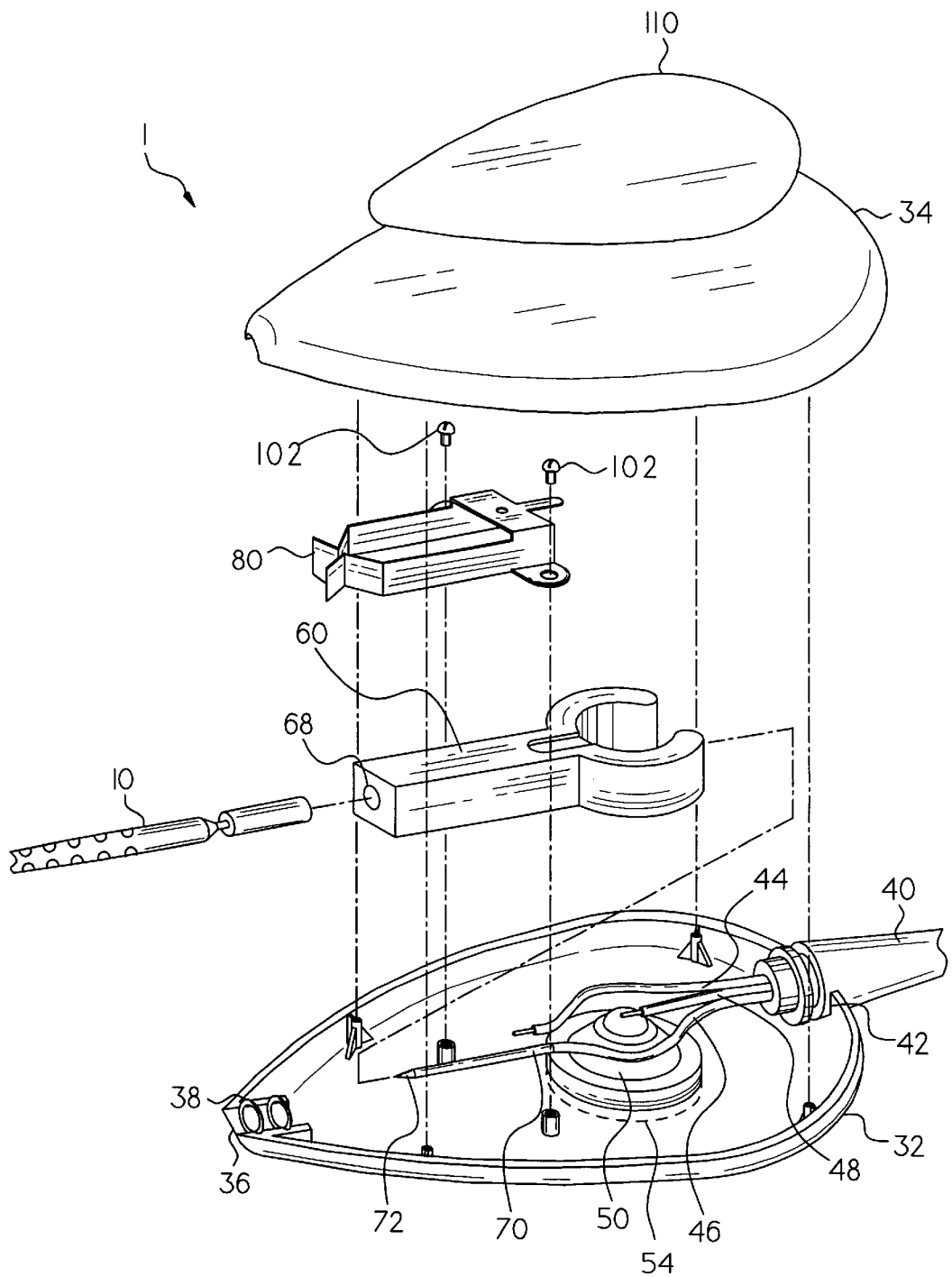
FIG. 5 is a perspective, exploded view highlighting the individual components of the sleeve and wire system of the subject invention.

FIG. 2 is a top perspective view and FIG. 3 is a top view illustrating the reusable housing 30, and specifically the bottom half 32 of housing 30, of the subject invention. Housing 30 is teardrop shaped to facilitate handling, especially when the user holds housing 30 while inserting safety cap 10 into housing 30. The top half 34 of housing 30 is shown in FIG. 5. Top half 34 and bottom half 32 of housing 30 have respective pins and holes to create a snap-fit connection forming the entire housing 30 upon engagement.

Housing 30 defines an aperture 36 in which are disposed one or more rings 38. Safety cap 10 can be inserted into aperture 36 and through rings 38 without regard to or restrictions relative to orientation. During insertion, rings 38 function to wipe safety cap 10 free of debris, moisture, and other undesirable contaminants. Rings 38 also function as a partial stop, upon engagement with groove 20 in safety cap 10, releasably holding safety cap 10 in housing 30.

In a preferred embodiment, two rings 38 are provided. The first ring 38 is a rubber O-ring that performs the wiping function. The second ring 38 performs the retention function upon engagement with groove 20. Elements alternative to the second ring 38 might also perform the retention function, such as a C-shaped clamp, a tilted circular spring, or a spring-loaded clamp—each designed to engage groove 20 in safety cap 10 and releasably hold safety cap 10 in housing 30.

As shown in FIG. 2, retention groove 20 is provided on grip segment 12 of safety cap 10. Accordingly, the retention element is positioned near aperture 36 of housing 30. Retention groove 20 could also be provided on tip segment 14 of safety cap 10. In that case, the retention element would have to be positioned further away from aperture 36, into housing 30.

Figure 7:
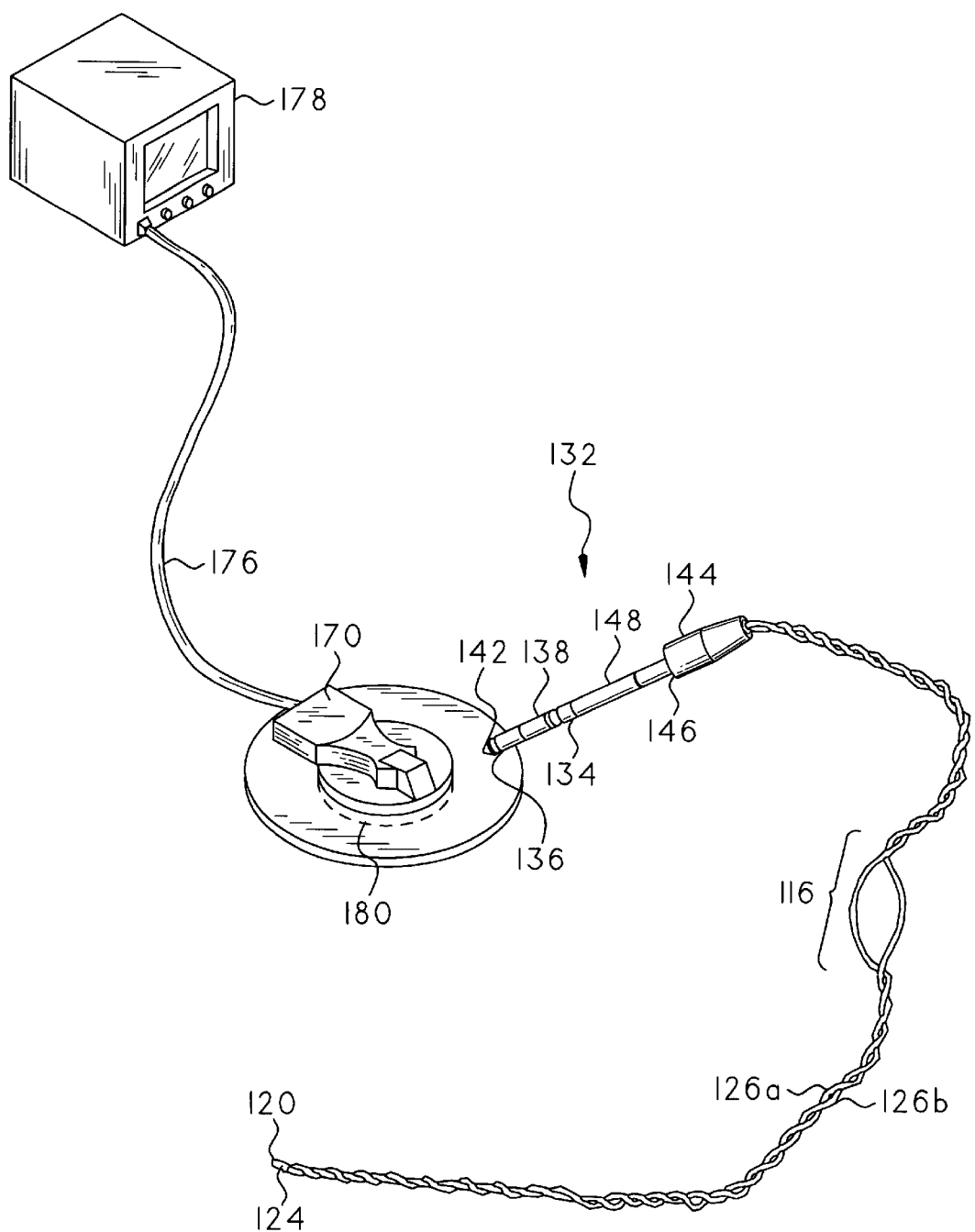
FIG. 7 is a perspective view of the connector of the conventional fetal spiral electrode system, illustrating that component in combination with several conventional elements.

Housing 30 also defines an opening 42 which may, but need not, be disposed opposite aperture 36. The trunk cable 40 connected to the remote fetal monitor 178 (see FIG. 7) can be inserted into opening 42. Trunk cable 40 typically has three, separate wires 44, 46, 48, and may also be shielded. Central ground wire 48 is connected to a snap 50 affixed to bottom half 32 of housing 30. Snap 50 engages a ground electrode 54 (see FIG. 5) located on the underside of bottom half 32 opposite snap 50. Ground electrode 54 is held in position, typically against a mother's leg. Ground electrode 54 can also be positioned against a mother's abdomen. For convenience, housing 30 may be attached to the patient via adhesive placed on one side of ground electrode 54, rendering ground electrode 54 a self-adhesive ground electrode and avoiding the need for a separate leg plate strap. Preferably, ground electrode 54 has a large surface area to assure adherence to the patient. Snap 50 is sized to allow a variety of alternate electrodes to be incorporated as ground electrode 54. Although not required, a separate strap may be used to facilitate attachment of housing 30 to the patient (i.e., the mother).

Housing 30 is rotatable relative to ground electrode 54 in either the clockwise or counterclockwise direction. This rotation allows housing 30 to be oriented into any desired angular orientation. The rotatable connection helps to avoid inadvertent disconnection of safety cap 10 from housing 30 when, for instance, a patient or caregiver brushes against the twisted wire pair 6, 8; housing 30; or trunk cable 40.

A nonconductive (molded) Y-shaped guide 60 is also provided in housing 30. Guide 60 has a central column 62 and two branches 64, 66. Branches 64, 66 engage and at least partially encircle snap 50, thereby supporting housing 30 and protecting the electrical connection between snap 50 and ground wire 48. An alignment channel 68 is provided in the end of guide 60. Alignment channel may be a bore in guide 60. At least the forward portion of tip segment 14 of safety cap 10 enters alignment channel 68 upon full insertion of safety cap 10 into housing 30. Alignment channel 68 of guide 60 helps to prevent over-insertion of safety cap 10 in housing 30. If retention groove 20 is provided on tip segment 14 of safety cap 10, the retention element (e.g., second ring 38) may be disposed on central column 62 of guide 60.

A conductive axial contact element 70 is also provided in housing 30. Axial contact element 70 is connected on one end to maternal wire 46 of trunk cable 40 and, as shown in the example illustrated in the drawing, may be a spring-loaded probe or "pogo pin." On its end opposite wire 46, the probe may have a sharp point 72. The probe is hollow and encases a spring (not shown) which biases sharp point 72 outward from the hollow probe. Axial contact element 70 is aligned with alignment channel 68 of guide 60 so that, when tip segment 14 of safety cap 10 enters alignment channel 68 upon full insertion of safety cap 10 into housing 30, the end (e.g., sharp point 72) of axial contact element (e.g., pogo pin) 70 axially enters recessed end 24 of tip segment 14 and makes electrical contact with the bare and exposed end of wire 8, which engages the maternal electrode, of the twisted wire pair. Thus, alignment channel 68 of guide 60 assures proper alignment between axial contact element 70 and wire 8 disposed in tip segment 14.

Figure 4:
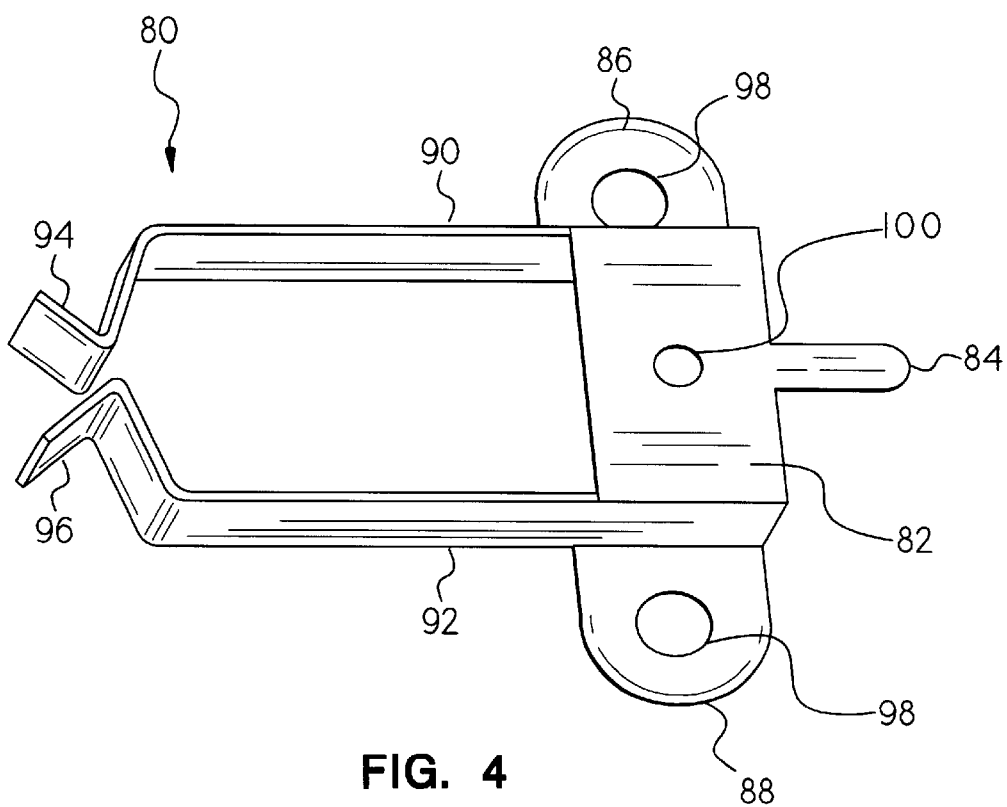
FIG. 4 is a detailed, perspective view of the radial contact element according to the present invention.

Finally, a conductive radial contact element 80 is provided in housing 30. As shown in the example illustrated in FIG. 4, radial contact element 80 may be a cantilever beam 80. The cantilever beam has a central body 82 from which extends longitudinally a head 84 and from which extend transversely two flanges 86, 88. Head 84 is connected to fetal wire 44 of trunk cable 40. Also extending from body 82 are a pair of arms 90, 92, each of which ends in a flexible, V-shaped finger 94, 96, respectively. A hole 98 is provided in each flange 86, 88 to receive a fastening member 102 (e.g., a screw, bolt, or the like) securing the cantilever beam to housing 30. A hole 100 in body 82 engages a projection 104 on guide 60 to help align the cantilever beam with respect to guide 60 within housing 30.

Recessed end 24 of tip segment 14 of safety cap 10 engages and separates flexible fingers 94, 96 of radial contact element 80 as safety cap 10 is inserted into housing 30. When safety cap 10 is fully inserted in housing 30, ring 38 engages groove 20 on safety cap 10 and the end of axial contact element 70 engages wire 8 disposed in tip segment 14. Substantially simultaneously, fingers 94, 96 of radial contact element 80 radially clamp onto exposed portion 18 of conductive sleeve 16, to which wire 6 of the twisted wire pair is attached. The engagement between fingers 94, 96 and conductive sleeve 16 may be sufficiently strong to further releasably secure safety cap 10 in housing 30 and help to prevent over-insertion of safety cap 10 in housing 30. Moreover, audible and tactile indications are provided to the user when safety cap 10 is properly engaged in housing 30. FIGS. 2 and 3 illustrate safety cap 10 as fully inserted into housing 30.

Upon full insertion of safety cap 10 into housing 30, three separate electrical paths are created. The first path is from (a) ground electrode 54 located on the underside of bottom half 32 of housing 30 opposite snap 50 and held in position against a mother's leg, to (b) snap 50 engaging ground electrode 54, to (c) ground wire 48 connected to snap 50, and to (d) remote monitor 178 through trunk cable 40. The second path is from (a) fetal spiral electrode 120 (see FIG. 6) affixed to the fetus, to (b) wire 6 of the twisted wire pair that engages fetal spiral electrode 120, to (c) conductive sleeve 16 disposed within grip segment 12 and to which wire 6 is attached, to (d) radial contact element 80 which radially clamps onto exposed portion 18 of conductive sleeve 16, to (e) fetal wire 44 connected to radial contact element 80, and to (f) remote monitor 178 through trunk cable 40. The third path is from (a) maternal reference electrode 122 (see FIG. 6) proximate fetal spiral electrode 120 inside the mother, to (b) wire 8 of the twisted wire pair that engages maternal reference electrode 122, to (c) the end of axial contact element 70 which axially engages wire 8, to (d) maternal wire 46 connected to axial contact element 70, and to (e) remote monitor 178 through trunk cable 40.

Noteworthy are the orientations of the electrical contacts made with fetal electrode wire 6 and with maternal reference wire 8. Wire 6 is connected to conductive sleeve 16, and radial contact element (e.g., cantilever beam) 80 clamps radially (or in a perpendicular direction) onto exposed portion 18 of conductive sleeve 16. In contrast, wire 8 engages axial contact element (e.g., pogo pin) 70 axially (or in a longitudinal direction). The two connections are also in separate planes, separated at least by the combined thickness of conductive sleeve 16 and the insulation around wire 8. Thus, the connections of wires 6, 8 have optimum separation and orientation that function to prevent short circuits—especially in the surrounding environment of conductive fluid.

FIG. 5 is a perspective, exploded view highlighting the individual components of the sleeve and wire system 1 of the subject invention. A label 110 may be affixed to housing 30 to identify the device and to provide information helpful to the user. Sleeve and wire system 1 electrically and mechanically connects wires 6, 8 of the twisted wire pair with trunk cable 40 of remote fetal monitor 178. Housing 30 protects such connection, especially from fluid contamination.

In using the sleeve and wire system 1 of the present invention, a caregiver inserts the forward end of curved guide tube or introducer 140 through the mother's vagina and cervix until the forward end of guide tube 140 makes contact with the fetal head or other portion of the fetus. Holding the forward end of guide tube 140 stationary, the caregiver then pushes the rear end of flexible drive rod or drive tube 130 forward until fetal spiral electrode 120 at the forward end of the wire 6 of the twisted wire pair makes contact with the fetal epidermis. The forward end of the other wire 8 attaches to spade-like maternal electrode 122 which is electrically isolated from fetal spiral electrode 120.

The caregiver then rotates flexible drive tube 130 clockwise about one full turn while maintaining the forward end of guide tube 140 against the fetal head. This action will screw fetal spiral electrode 120 into the fetal epidermis. Thereafter, the caregiver grasps the outer ends of drive tube 130 and guide tube 140 and slides tubes 130, 140 as a unit off wires 6, 8 and safety cap 10, leaving only bipolar electrodes 120, 122 and two twisted wires 6, 8 within the mother. The outside diameter of safety cap 10 is smaller than the inside diameter of drive tube 130 which, in turn, is smaller than the inside diameter of guide tube 140. Thus, guide tube 140 and drive tube 130 may be pulled together over safety cap 10 and thereby removed from the twisted wire pair.

After removal of tubes 130, 140, safety cap 10 is free and accessible for its insertion into housing 30. Such insertion creates the three separate electrical paths discussed above and thereby connects the three electrodes (fetal 120, maternal 122, and ground 54) with remote monitor 178. A galvanic potential difference may then be measured between bipolar electrodes 120, 122.

Sleeve and wire system 1 of the subject invention offers ease of use. Drive tube 130 and guide tube 140 can be removed by the user in one step, saving time. No additional steps are required. Connection between wires 6, 8 and trunk cable 40 is fast and accomplished without regard to orientation. Safety cap 10 and housing 30 permit connection and re-connection of electrodes 120, 122 several times during labor. Sleeve and wire system 1 is and, more specifically, the connections between safety cap 10 and housing 30 and between trunk cable 40 and housing 30 are, sufficiently robust to withstand fluid contact (such as by splashing if not immersion) for a minimum of twelve hours. Sleeve and wire system 1 of the subject invention also offers reliability: excellent signal quality and signal acquisition throughout labor, resulting in accurate and consistent fetal heart rate tracings by monitor 178.

Housing 30 provides a reliable electrical and mechanical interface between electrodes 120, 122 and monitor 178 throughout labor, resulting in accurate and consistent fetal heart rate tracings. Housing 30 has a relatively low profile and low weight. Housing 30 also has smooth and rounded edges. These features maximize patient comfort.

Other than monitor 178, the components of sleeve and wire system 1 are sufficiently inexpensive to permit single use followed by disposal (i.e., the components are disposable). Caregivers may wish to clean and sterilize, then reuse, trunk cable 40. If so, trunk cable 40 can be cleaned and disinfected after each use with hand soap, isopropyl alcohol, chlorine bleach (1:10 with water), or 2% glutaraldehyde solution. The cost of the components of sleeve and wire system 1 is further reduced because complex components, such as a printed circuit board, are not required.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A fetal electrode sleeve and wire interconnect system for transmitting signals indicative of fetal heart rate from a fetus inside a mother through a cable to a monitor external to the mother, the system comprising:
    a holder having a fetal electrode on one end and a maternal reference electrode on its opposite end;
    a ground electrode;
    a safety cap having a retention groove, a grip, a tip opposite the grip with a shroud defining both a safety cap terminus and an end recessed relative to the terminus, and a conductive sleeve, the conductive sleeve including a first end enclosed by the grip, a second end enclosed by the tip, and an intermediate exposed portion enclosed by neither the grip nor the tip;
    a twisted wire strand including a pair of insulated wires each having a first end and a second end, the first ends of the wires respectively connected to the fetal electrode and the maternal reference electrode, the second end of one wire attached to the first end of the conductive sleeve and the other wire being disposed inside the conductive sleeve, extending beyond the second end of the conductive sleeve, and terminating at its second end as a bare and exposed wire at the recessed end of the tip so that the second end of the wire is protected within the shroud; and
    a housing receiving the safety cap without restriction relative to the orientation of the safety cap, facilitating electrical connection between the wires and the cable, and being attached to the ground electrode.

2. The fetal electrode sleeve and wire interconnect system of claim 1 further comprising a drive mechanism imparting rotation and translation to the holder to secure attachment of the fetal electrode to the fetus, and an introducer disposed around at least a portion of the drive mechanism, adapted to be comfortably inserted through the cervix of the mother, and within which the holder is slidably and rotatably disposed.

3. The fetal electrode sleeve and wire interconnect system of claim 1 wherein the housing has an aperture, the system further comprising a ring positioned in the aperture of the housing and through which the safety cap is inserted into the housing, the ring wiping the safety cap upon insertion.

4. The fetal electrode sleeve and wire interconnect system of claim 3 wherein the ring is a rubber O-ring.

5. The fetal electrode sleeve and wire interconnect system of claim 3 wherein the housing has an opening receiving the cable.

6. The fetal electrode sleeve and wire interconnect system of claim 1 wherein the housing has a retaining element engaging the retention groove in the safety cap upon insertion of the safety cap in the aperture of the housing and releasably holding the safety cap in the housing.

7. The fetal electrode sleeve and wire interconnect system of claim 1 wherein the grip of the safety cap has a plurality of cutouts disposed opposite the tip, the cutouts providing strain relief to and increasing the flexibility of the safety cap and being adapted to facilitate handling of the safety cap by the user.

8. The fetal electrode sleeve and wire interconnect system of claim 1 wherein the housing has a snap connected to the ground electrode, the housing rotating without restriction relative to the ground electrode.

9. The fetal electrode sleeve and wire interconnect system of claim 8 wherein the ground electrode is secured to the mother.

10. The fetal electrode sleeve and wire interconnect system of claim 9 wherein the ground electrode has an adhesive securing the ground electrode to the mother.

11. The fetal electrode sleeve and wire interconnect system of claim 8 wherein the snap is attached to a ground lead of the cable.

12. The fetal electrode sleeve and wire interconnect system of claim 8 wherein the housing has a guide which includes an alignment channel receiving and aligning the tip of the safety cap upon insertion of the safety cap into the housing.

13. The fetal electrode sleeve and wire interconnect system of claim 12 wherein the housing has an axial contact element aligned in the channel of the guide, the axial contact element axially engaging the tip of the safety cap and contacting the bare and exposed wire upon insertion of the safety cap into the housing.

14. The fetal electrode sleeve and wire interconnect system of claim 13 wherein the axial contact element is attached to a maternal lead of the cable.

15. The fetal electrode sleeve and wire interconnect system of claim 1 wherein the housing has a radial contact element including at least one finger, the finger radially engaging the intermediate exposed portion of the conductive sleeve of the safety cap upon insertion of the safety cap into the housing, thereby electrically contacting the conductive sleeve.

16. The fetal electrode sleeve and wire interconnect system of claim 15 wherein the radial contact element is attached to a fetal lead of the cable.

17. A fetal electrode sleeve and wire interconnect system for transmitting signals indicative of fetal heart rate from a fetus inside a mother through a cable to a monitor external to the mother, the system comprising:
  a holder having a fetal electrode on one end and a maternal reference electrode on its opposite end;
  a ground electrode;
  a safety cap having a retention groove, a grip, a tip opposite the grip with a shroud defining both a safety cap terminus and an end recessed relative to the terminus, and a conductive sleeve, the conductive sleeve including a first end enclosed by the grip, a second end enclosed by the tip, and an intermediate exposed portion enclosed by neither the grip nor the tip;
  a twisted wire strand including a pair of insulated wires each having a first end and a second end, the first ends of the wires respectively connected to the fetal electrode and the maternal reference electrode, the second end of one wire attached to the first end of the conductive sleeve and the other wire being disposed inside the conductive sleeve, extending beyond the second end of the conductive sleeve, and terminating at its second end as a bare and exposed wire at the recessed end of the tip so that the second end of the wire is protected within the shroud; and
  a housing having:
    (a) an aperture receiving the safety cap without restriction relative to the orientation of the safety cap,
    (b) an opening receiving the cable,
    (c) a retaining element engaging the retention groove in the safety cap upon insertion of the safety cap in the aperture of the housing and releasably holding the safety cap in the housing,
    (d) a snap connected to the ground electrode and attached to a ground lead of the cable, the housing rotating without restriction relative to the ground electrode,
    (e) a guide which includes an alignment channel receiving and aligning the tip of the safety cap upon insertion of the safety cap into the housing,
    (f) an axial contact element aligned in the channel of the guide and attached to a maternal lead of the cable, the axial contact element axially engaging the tip of the safety cap and contacting the bare and exposed wire upon insertion of the safety cap into the housing, and
    (g) a radial contact element including at least one finger, the finger radially engaging the intermediate exposed portion of the conductive sleeve of the safety cap upon insertion of the safety cap into the housing, thereby electrically contacting the conductive sleeve, the radial contact element also being attached to a fetal lead of the cable.

18. The fetal electrode sleeve and wire interconnect system of claim 17 further comprising a drive mechanism imparting rotation and translation to the holder to secure attachment of the fetal electrode to the fetus, and an introducer disposed around at least a portion of the drive mechanism, adapted to be comfortably inserted through the cervix of the mother, and within which the holder is slidably and rotatably disposed.

19. The fetal electrode sleeve and wire interconnect system of claim 17 further comprising a ring positioned in the aperture of the housing and through which the safety cap is inserted into the housing, the ring wiping the safety cap upon insertion.

20. The fetal electrode sleeve and wire interconnect system of claim 19 wherein the ring is a rubber O-ring.

21. The fetal electrode sleeve and wire interconnect system of claim 17 wherein the grip of the safety cap has a plurality of cutouts disposed opposite the tip, the cutouts providing strain relief to and increasing the flexibility of the safety cap and being adapted to facilitate handling of the safety cap by the user.

22. The fetal electrode sleeve and wire interconnect system of claim 17 wherein the ground electrode is secured to the mother.

23. The fetal electrode sleeve and wire interconnect system of claim 22 wherein the ground electrode has an adhesive securing the ground electrode to the mother.

24. A fetal electrode sleeve and wire interconnect system for monitoring signals indicative of fetal heart rate from a fetus inside a mother, the system comprising:
  a cable having a maternal lead, a fetal lead, and a ground lead;
  a holder having a fetal electrode on one end and a maternal reference electrode on its opposite end;
  a ground electrode;
  a safety cap having a retention groove, a grip, a tip opposite the grip with a shroud defining both a safety cap terminus and an end recessed relative to the terminus, and a conductive sleeve, the conductive sleeve including a first end enclosed by the grip, a second end enclosed by the tip, and an intermediate exposed portion enclosed by neither the grip nor the tip;
  a twisted wire strand including a pair of insulated wires each having a first end and a second end, the first ends of the wires respectively connected to the fetal electrode and the maternal reference electrode, the second end of one wire attached to the first end of the conductive sleeve and the other
  wire being disposed inside the conductive sleeve, extending beyond the second end of the conductive sleeve, and terminating at its second end as a bare and exposed wire at the recessed end of the tip so that the second end of the wire is protected within the shroud;

a housing having:
  (a) an aperture receiving the safety cap without restriction relative to the orientation of the safety cap,
  (b) an opening receiving the cable,
  (c) a retaining element engaging the retention groove in the safety cap upon insertion of the safety cap in tile aperture of the housing and releasably holding the safety cap in the housing,
  (d) a snap connected to the ground electrode and attached to the ground lead of the cable, the housing rotating without restriction relative to the ground electrode,
  (e) a guide which includes a channel receiving and aligning the tip of the safety cap upon insertion of the safety cap into the housing,
  (f) an axial contact element aligned in the channel of the guide and attached to the maternal lead of the cable, the axial contact element axially engaging the tip of the safety cap and contacting the bare and exposed wire upon insertion of the safety cap into the housing, and
  (g) a radial contact element including at least one finger, the finger radially engaging the intermediate exposed portion of the conductive sleeve of the safety cap upon insertion of the safety cap into the housing, thereby electrically contacting the conductive sleeve, the radial contact element also being attached to the fetal lead of the cable; and
a monitor connected to the cable.

25. The fetal electrode sleeve and wire interconnect system of claim 24 further comprising a drive mechanism imparting rotation and translation to the holder to secure attachment of the fetal electrode to the fetus, and an introducer disposed around at least a portion of the drive mechanism, adapted to be comfortably inserted through the cervix of the mother, and within which the holder is slidably and rotatably disposed.

26. The fetal electrode sleeve and wire interconnect system of claim 24 further comprising a ring positioned in the aperture of the housing and through which the safety cap is inserted into the housing, the ring wiping the safety cap upon insertion.

27. The fetal electrode sleeve and wire interconnect system of claim 26 wherein the ring is a rubber O-ring.

28. The fetal electrode sleeve and wire interconnect system of claim 24 wherein the grip of the safety cap has a plurality of cutouts disposed opposite the tip, the cutouts providing strain relief to and increasing the flexibility of the safety cap and being adapted to facilitate handling of the safety cap by the user.

29. The fetal electrode sleeve and wire interconnect system of claim 24 wherein the ground electrode is secured to the mother.

30. The fetal electrode sleeve and wire interconnect system of claim 29 wherein the ground electrode has an adhesive securing the ground electrode to the mother.

* * * * *

UNITED STATES PATENT AND TRADEMARK OFFICE
CERTIFICATE OF CORRECTION

PATENT NO. : 6,321,103 B1
DATED : November 20, 2001
INVENTOR(S) : Edward Dowd et al.

It is certified that error appears in the above-identified patent and that said Letters Patent is hereby corrected as shown below:

<u>Title page,</u>
Item [56], References Cited, U.S. PATENT DOCUMENTS, please insert:

| | | |
|---|---|---|
| -- 4,209,020 | 06/24/80 | Nielsen |
| 5,445,537 | 08/29/95 | Abyzov |
| 5,341,812 | 08/30/94 | Allaire et al. |
| 5,404,876 | 04/11/95 | DiSabito et al. |
| 5,632,274 | 05/27/97 | Quedens et al. |
| 5,373,843 | 12/20/94 | Quedens et al. |
| 5,199,432 | 04/06/93 | Quedens et al. |
| 5,168,876 | 12/08/92 | Quedens et al. |
| 5,205,288 | 04/27/93 | Quedens et al. |
| 5,671,736 | 09/30/97 | Pettit et al. |
| 5,388,579 | 02/14/95 | Dowd et al. |
| 5,046,965 | 09/10/91 | Neese et al. |
| 5,062,426 | 11/05/91 | Ulbrich et al. |
| 5,615,674 | 04/01/97 | Maurer |
| 5,377,677 | 01/03/95 | Dowd et al. |
| 5,680,859 | 10/28/97 | Urion et al. |
| 5,197,472 | 03/30/93 | DiSabito |
| 4,644,957 | 02/24/87 | Ricciardelli et al. |
| Re.28,990 | 10/05/76 | Hon et al. -- |

<u>Column 1,</u>
Line 6, delete "deliver" and insert -- delivery --;

UNITED STATES PATENT AND TRADEMARK OFFICE
CERTIFICATE OF CORRECTION

PATENT NO. : 6,321,103 B1
DATED : November 20, 2001
INVENTOR(S) : Edward Dowd et al.

It is certified that error appears in the above-identified patent and that said Letters Patent is hereby corrected as shown below:

Column 7,
Line 24, after the word "channel" insert -- 68 --;

Column 13,
Line 6, delete "tile" and insert -- the --;

Signed and Sealed this

First Day of October, 2002

*Attest:*

*Attesting Officer*

JAMES E. ROGAN
*Director of the United States Patent and Trademark Office*